(12) United States Patent
Schertiger

(10) Patent No.: US 11,819,446 B2
(45) Date of Patent: *Nov. 21, 2023

(54) OSTOMY APPLIANCE COUPLING SYSTEM WITH A COUPLING PART HAVING AN ENCLOSED VOLUME OF AIR

(71) Applicant: Coloplast A/S, Humlebaek (DK)

(72) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 93 days.

This patent is subject to a terminal disclaimer.

(21) Appl. No.: 17/534,557

(22) Filed: Nov. 24, 2021

(65) Prior Publication Data

US 2022/0079804 A1    Mar. 17, 2022

Related U.S. Application Data

(63) Continuation of application No. 15/769,743, filed as application No. PCT/DK2016/050336 on Oct. 19, 2016, now Pat. No. 11,213,420.

(30) Foreign Application Priority Data

| Oct. 20, 2015 | (DK) | .......................... | PA 2015 70680 |
| Oct. 20, 2015 | (DK) | .......................... | PA 2015 70682 |
| May 20, 2016 | (DK) | .......................... | PA 2016 70340 |
| Aug. 18, 2016 | (DK) | .......................... | PA 2016 70633 |

(51) Int. Cl.
*A61F 5/448*    (2006.01)
*A61F 5/445*    (2006.01)
*A61F 5/44*    (2006.01)

(52) U.S. Cl.
CPC .............. *A61F 5/448* (2013.01); *A61F 5/445* (2013.01); *A61F 5/44* (2013.01)

(58) Field of Classification Search
CPC ............. A61F 5/448; A61F 5/445; A61F 5/44
See application file for complete search history.

(56) References Cited

U.S. PATENT DOCUMENTS

| 2,221,321 A * 11/1940 | Foron | ..................... A61F 5/445 |
| | | 604/338 |
| 2,563,597 A * 8/1951 | Friedman | ................ A61F 5/445 |
| | | 604/339 |
| 2,808,830 A * 10/1957 | Perry | ..................... A61F 5/445 |
| | | 604/343 |

(Continued)

FOREIGN PATENT DOCUMENTS

| EP | 1033119 A1 | 9/2000 |
| FR | 802823 A | 9/1936 |

(Continued)

*Primary Examiner* — Guy K Townsend
(74) *Attorney, Agent, or Firm* — Coloplast Corp., Coloplast A/S; Nick Baumann

(57) ABSTRACT

An ostomy appliance coupling system includes a first coupling part with a gas-impermeable layer forming an enclosed volume of air, with the gas-impermeable layer sealed to one of a sealing wafer and an ostomy bag. A second coupling part is connected to an opposite one of the sealing wafer and the ostomy bag. A depression in the second coupling part is shaped to receive and couple with a protruding member of the first coupling part to removably couple the ostomy bag to the sealing wafer.

10 Claims, 3 Drawing Sheets

(56) References Cited

U.S. PATENT DOCUMENTS

| | | | |
|---|---|---|---|
| 3,100,488 A * | 8/1963 | Orowan | A61F 5/448 604/342 |
| 3,878,847 A * | 4/1975 | Marsan | A61F 5/445 604/338 |
| 4,319,571 A * | 3/1982 | Winchell | A61F 5/445 604/342 |
| 4,419,100 A * | 12/1983 | Alexander | A61F 5/448 604/339 |
| 4,460,363 A * | 7/1984 | Steer | A61F 5/448 604/339 |
| 4,642,107 A * | 2/1987 | Arnone | A61F 5/448 604/342 |
| 4,648,875 A * | 3/1987 | Ferguson | A61F 5/448 604/339 |
| 4,846,798 A | 7/1989 | Holtermann et al. | |
| 4,850,985 A * | 7/1989 | Edwards | A61F 5/448 604/339 |
| 4,973,323 A * | 11/1990 | Kaczmarek | A61F 5/448 604/277 |
| 5,167,651 A * | 12/1992 | Leise, Jr | A61F 5/448 604/339 |
| 5,269,773 A * | 12/1993 | Vidal | A61F 5/448 604/338 |
| 5,346,482 A * | 9/1994 | Metz | A61F 5/448 604/338 |
| 5,364,379 A * | 11/1994 | Ozenne | F16L 37/008 604/344 |
| 5,496,297 A | 3/1996 | Olsen | |
| 5,785,695 A * | 7/1998 | Sato | A61F 5/445 604/338 |
| 6,106,507 A * | 8/2000 | Botten | A61F 5/448 604/338 |
| 7,976,522 B2 * | 7/2011 | Hansen | A61F 5/442 604/277 |
| 8,652,112 B2 * | 2/2014 | Johannison | A61F 5/443 604/338 |
| 11,213,420 B2 * | 1/2022 | Schertiger | A61F 5/448 |
| 2004/0059306 A1 * | 3/2004 | Tsal | A61F 5/4404 604/332 |
| 2007/0027434 A1 * | 2/2007 | Pedersen | A61F 5/441 604/338 |
| 2007/0219514 A1 * | 9/2007 | Strobech | A61F 5/441 604/339 |
| 2008/0154220 A1 * | 6/2008 | Gaffney | A61F 5/445 604/339 |
| 2010/0137821 A1 * | 6/2010 | Hansen | A61F 5/442 604/338 |
| 2010/0191202 A1 | 7/2010 | Hogard et al. | |
| 2010/0241093 A1 * | 9/2010 | Hooper | A61F 5/445 604/339 |
| 2011/0071485 A1 * | 3/2011 | Foley | A61F 5/448 604/344 |
| 2012/0323193 A1 * | 12/2012 | Johannison | A61F 5/443 604/344 |
| 2015/0359658 A1 | 12/2015 | Leise, Jr. | |
| 2018/0311067 A1 * | 11/2018 | Schertiger | A61F 5/448 |

FOREIGN PATENT DOCUMENTS

| | | |
|---|---|---|
| GB | 2023007 A1 | 12/1979 |
| WO | 9218074 A1 | 10/1992 |
| WO | 2004105657 A2 | 12/2004 |

* cited by examiner

OSTOMY APPLIANCE COUPLING SYSTEM WITH A COUPLING PART HAVING AN ENCLOSED VOLUME OF AIR

BRIEF SUMMARY

Embodiments provide a coupling system for an ostomy appliance comprising a sealing wafer and a collecting bag. The coupling system comprises a first coupling part and a second coupling part. The first and second coupling parts each encircle a stoma-receiving opening. The first and second coupling parts are configured to connect the sealing wafer to the collecting bag. The first coupling part comprises a first base portion, a second base portion and a connecting portion extending between the first and second base portions. The first base portion is arranged radially closer to the stoma-receiving opening than the second base portion. The first coupling part comprises an enclosed volume of air. The enclosed volume of air is at least partially enclosed by the first base portion, the second base portion and the connecting portion.

BACKGROUND

In connection with surgery for a number of diseases in the gastro-intestinal tract, one of the consequences in many cases is that the user is left with an abdominal stoma, such as a colostomy or an ileostomy in the abdominal wall for the discharge of visceral content. The discharge of visceral content, including intestinal gases, cannot be regulated at will. For that purpose, the user will have to rely on an ostomy appliance to collect the material emerging from such opening, in a bag later emptied and/or discarded at a suitable time.

In many cases, the user will attach a base plate or sealing wafer to the surface of the skin surrounding the opening. This base plate then may serve as an attachment anchor for an ostomy bag that attaches to the base plate. The attachment between the base plate and the ostomy bag serves at least to bear the load of the ostomy bag and to form a seal between the base plate and the ostomy bag. These two purposes put different constraints on the attachment.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other.

Like reference numerals designate corresponding similar parts.

DETAILED DESCRIPTION

Figure 1:
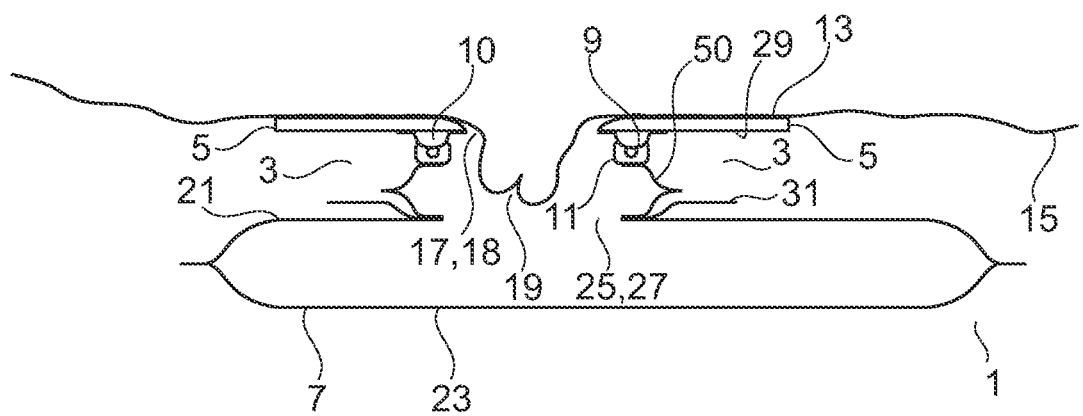
FIG. 1 illustrates a schematic cross-sectional side view of an embodiment of an ostomy appliance.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments provide an ostomy appliance having improved sealing properties to prevent leakage. Embodiments provide an ostomy appliance configured with separated sealing and load bearing capabilities.

Accordingly, in a first aspect, embodiments provide a coupling system for an ostomy appliance comprising a sealing wafer and a collecting bag, the coupling system comprising a first coupling part and a second coupling part, the first and second coupling parts each encircling a stoma-receiving opening, the first and second coupling parts being configured to connect the sealing wafer to the collecting bag, wherein the first coupling part comprises a first base portion, a second base portion and a connecting portion extending between the first and second base portions, the first base portion being arranged radially closer to the stoma-receiving opening than the second base portion, and wherein the first coupling part comprises an enclosed volume of air, the enclosed volume of air being at least partially enclosed by the first base portion, the second base portion and the connecting portion.

The first coupling part and the second coupling part are configured to connect the collecting bag to the sealing wafer. During normal use, the sealing wafer is attached to the skin of the user and the collecting bag is connected to the sealing wafer. The first and second coupling parts may be arranged so that the first coupling part forms part of the sealing wafer and the second coupling part forms part of the collecting bag, or so that the first coupling part forms part of the collecting bag and the second coupling part forms part of the sealing wafer, in both cases, visceral content from a user may be received by the ostomy appliance through the stoma-receiving openings of the first and second coupling parts.

The volume of air at least partially enclosed by the first coupling part allows the first coupling part to have a mechanical flexibility. The mechanical flexibility can be achieved by appropriate choice of material and material thickness for the first coupling part. In the present context, the term mechanical flexibility is to be understood as a mechanical flexibility of the structure being large enough to allow an average person to deform and/or bend the structure with the fingers. Accordingly, the enclosed volume of air may allow the first coupling part to deform in order to provide additional flexibility in relation to the second coupling part and/or the user's body. For instance, the shape of the user's body often changes when the user moves the body during everyday activities such as bending over, standing up, twisting the body, jumping, etc. The ability of the first coupling part to conform to such movements provides improved sealing between the ostomy appliance and the user's skin.

In embodiments, the first and second coupling parts are configured to be gas and liquid impermeable so as to form a gas and liquid impermeable seal when connected.

The sealing wafer is provided with a proximal surface configured for attachment to the user's skin. In embodiments, the proximal surface of the sealing wafer comprises an adhesive for attachment to the skin. In embodiments, the adhesive is a pressure sensitive adhesive. In embodiments, the first coupling part or the second coupling part is arranged on a distal surface of the sealing wafer.

FIG. 1 illustrates a schematic cross-sectional side view of an embodiment of an ostomy appliance 1 with a coupling system 3 according to a first aspect. The coupling system 3 is configured to connect the sealing wafer 5 to the collecting bag 7 and includes a first coupling part 9 and a second coupling part 11. The first coupling part 9 includes an enclosed volume of aft 10.

The sealing wafer 5 defines a proximal surface 13 provided with an adhesive adapted for engagement to a skin surface 15 of a user and therefore presents skin-friendly characteristics. In one embodiment, the adhesive is an adhesive including polyisobutylene, styrene-isoprene-styrene and hydrocolloids such as, but not limited to, the types of adhesives disclosed in WO 99/11302. In embodiments, the sealing wafer 5 defines a first stoma-receiving opening 17, In embodiments, the first stoma-receiving opening 17 of the sealing wafer 5 coincides with a second stoma-receiving opening 18 of the first coupling part 9. In one embodiment, the sealing wafer 5 is adapted to allow the first stoma-receiving opening 17 to be customized to a size and shape of a user's individual stoma 19.

The collecting bag 7 includes a proximal wall 21 and a distal wall 23. The walls 21, 23 are joined along their individual outer peripheries to form a collecting volume inside the collecting bag 7 for stomal output. The walls 21, 23 are made of and liquid impermeable foil-material (for example of polyethylene (PE), polyvinyl-chloride (PVC) or ethylene-vinyl-acetate (EVA)) that is welded around the edges of the rim so as to form a pouch defining a waste collection chamber. In some embodiments, the collecting bag 7 includes a foldable outlet (not shown) at a lower portion of the collecting bag 7 for intermittent emptying of stomal output from the collecting bag 7. The collecting bag 7 includes a waste inlet opening 25 in the proximal wall 21 of the collecting bag 7 for receiving stomal output. The waste inlet opening 25 coincides with a third stoma-receiving opening 27 of the second coupling part 11.

The first and second coupling parts 9, 11 of the embodiment illustrated in FIG. 1 are configured to detachably connect. In present context, detachably connect means that the first coupling part 9 and the second coupling part 11 can be connected and separated from each other without breaking the coupling system 3. In embodiments, the first and second coupling parts 9, 11 include resilient coupling members configured to form a mating couple. In embodiments, the resilient coupling members have complementary shapes that need to deform for the coupling members to change from being connected to disconnected and vice versa. In other embodiments, the first and second coupling parts 9, 11 are configured to fixedly connect. In present context, fixedly connect means that the first and second coupling parts 9, 11 cannot be separated from each other without breaking the coupling system 3 and rendering it useless.

Figure 2:
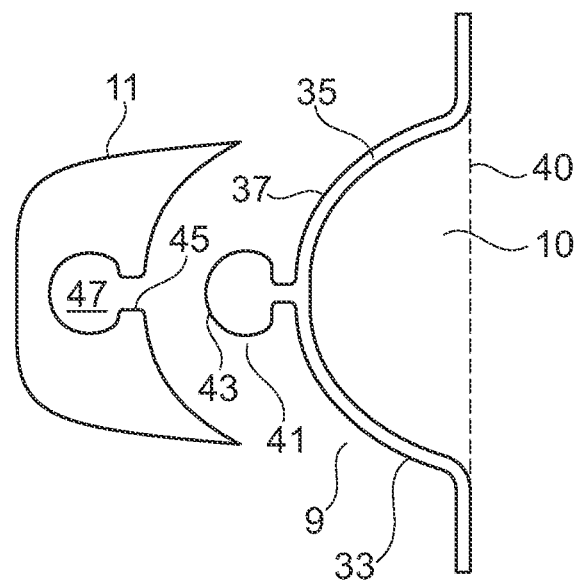
FIG. 2 illustrates a schematic of an enlarged cross-sectional view of embodiment of an ostomy appliance.

FIG. 2 illustrates a schematic of an enlarged cross-sectional view of one embodiment including first and second coupling parts 9, 11. The first coupling part 9 includes a first base portion 33, a second base portion 35 and a connecting portion 37. In embodiments, the first base portion 33 is arranged radially closer to the first stoma-receiving opening 17 (not shown) than the second base portion 35. The first base portion 33, second base portion 35 and connecting portion 37 partially enclose a volume of air 10. The dashed line 40 indicates a further perimeter of the enclosed volume of air 10. In embodiments, the further perimeter 40 forms part of the first coupling part 9. In embodiments, the further perimeter 40 is defined by a surface of the sealing wafer 5 or the collecting bag 7.

Figure 3:
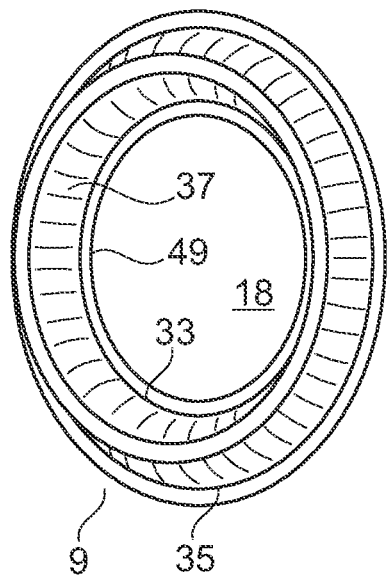
FIG. 3 illustrates an embodiment of an ostomy appliance.

FIG. 3 is a schematic, perspective view of a first coupling part 9 according to one embodiment. In FIG. 3, the second stoma-receiving opening 18 of the first coupling part 9 is arranged radially inward of a perimeter 49 defined by the first base portion 33.

Figure 4:
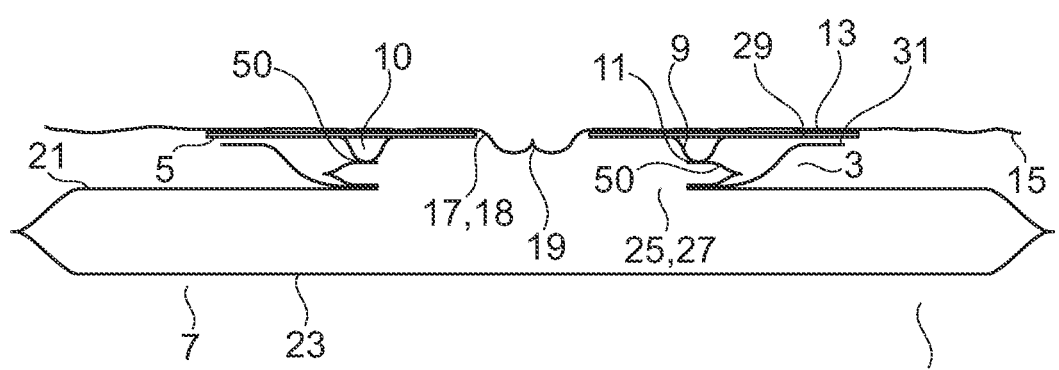
FIG. 4 illustrates a schematic cross-sectional side view of an embodiment of an ostomy appliance.

FIG. 4 illustrates a schematic cross-sectional side view of one embodiment of an ostomy appliance 1 with a coupling system 3, In the embodiment of FIG. 4, the coupling system 3 does not include resilient coupling members forming a mating couple. In the embodiment of FIG. 4, the first and second coupling parts 9, 11 are configured to connect by use of an adhesive. More specifically, an adhesive on a proximal surface of the second coupling part 11 is adapted to adhere to a distal side of the first coupling part 9. The adhesive allows the first and second coupling parts 9, 11 to detachably connect or fixedly connect.

In embodiments, a mechanical flexibility of the first coupling part allows the enclosed volume of air 10 to be compressed and/or deformed in response to an external pressure applied to the first coupling part.

Thereby, the enclosed volume of air 10 may be directly influenced by the external pressure applied to the first coupling part. Accordingly, the mechanical properties of the first coupling part are, at least in part, determined by the mechanical properties of the enclosed volume of air 10. This further enhances the ability of the first coupling part to conform to alternating shapes and avoid leakage.

In present context, the 'external pressure applied' is meant as the pressure applied by, e.g. the fingers of an average person. Accordingly, the mechanical flexibility of the first coupling part allows the enclosed volume of air 10 to be compressed and/or deformed in response to an external pressure applied by the fingers of an average person.

Appropriate materials for achieving the mechanical flexibility of the first coupling part comprise polymers. In one embodiment, an appropriate material comprises silicone. In one embodiment, it comprises silicone rubber. In one embodiment, the first coupling part comprises a heat cured elastomer. Other types of polymers are also appropriate. In one embodiment, the first coupling part has a Shore hardness in the range of 35A to 85A, more particularly 40A to 70A, more particularly 45A to 65A. By 'Shore hardness' is meant a hardness measured according to the ASTM D2240 standard with a type A durometer on the A scale. The thickness of the material may be chosen based on the flexibility of the material. Accordingly, a more flexible material may have a larger thickness than a less flexible material while still preserving a similar mechanical flexibility of the first coupling part, which allows the enclosed volume of air 10 to be compressed and/or deformed in response to an external pressure in the sense of the present context. Moreover, if in a first embodiment, the first coupling part is made from a material having a first Shore hardness and a first thickness, and in a second embodiment, the first coupling part is made from a material having a second Shore hardness and a second thickness, a similar mechanical flexibility of the two first coupling parts may be achieved even if the first Shore hardness is smaller than the second Shore hardness, if the first thickness is larger than the second thickness. In embodiments, these options provide for differentiating the firmness of the coupling parts, which in turn allows for adapting the attachment (and detachment) forces of the coupled parts to suit the physical capabilities of different users.

In embodiments, the enclosed volume of air 10 exerts an internal pressure on at least part of the first coupling part, and the internal pressure is configured to support at least part of the first coupling part when the first and second coupling parts are connected.

Thereby, the enclosed volume of air 10 contributes to the mechanical resilience of the first coupling part. Moreover, as the enclosed volume of air 10 is compressed, the shape of the first coupling part will depart from its initial shape. The compression causes the internal pressure of the enclosed volume of air 10 to increase, which works to restore the initial shape of the first coupling part. In embodiments, the enclosed volume of air 10 provides the first coupling part with an enhanced flexibility to make it bend and conform to the body of the user more easily. It also provides the first coupling part with sufficient mechanical resilience to minimize deformation in the use situation. Both of these effects, on their own and in combination, provide an improved sealing between the connected first and second coupling parts.

In the embodiment illustrated in FIG. 2, the first base portion 33, second base portion 35 and connecting portion 37 are made of a relatively flexible material having a Shore hardness in the range of 35A to 85A, which allows the enclosed volume of air 10 to be compressed and deformed in response to an external pressure applied to the first coupling part 9. A mechanical flexibility of the first coupling part 9 allows it to deform and adjust in response to movements of the user. The enclosed volume of air 10 will exert an internal pressure on the first base portion 33, second base portion 35 and connecting portion 37. The internal pressure supports at least these portions 33, 35, 37 when the first and second coupling parts 9, 11 are connected. Suitable materials for the first coupling part could be any type of polymer or other material that may produce mechanically flexible and gas-impermeable members. In the embodiment of FIG. 2, the first and second coupling parts 9, 11 are made from a heat cured elastomer having a Shore hardness of 65A made from silicone rubber.

In embodiments, the first coupling part comprises a first attachment portion and the second coupling part comprises a second attachment portion, wherein the first and second attachment portions combine to form a first attachment defining a first detachment force between the first and second coupling parts when the first and second coupling parts are connected.

Thereby, the attachment portions of the first and second coupling parts provide a detachment force. In one embodiment, the attachment portions are configured to provide a detachment force sufficient to carry the load of the collecting bag. In one embodiment, the detachment force is lower than what is required to carry the load of the collecting bag. In embodiments, the attachment portion of the first coupling part and/or the second coupling part are structurally different from the first and second base portions and/or the connecting portion, so as to have a different mechanical flexibility, different thickness, etc.

In the embodiment illustrated in FIG. 2, the first coupling part 9 includes a first attachment portion 41 in the form of a resilient coupling member including a protrusion 43, The second coupling part 11 includes a second attachment portion 45 in the form of a resilient coupling member including a depression 47 formed in the resilient coupling member. In embodiments, the shapes of the first and second attachment portions 41, 45 are configured to deform in order for the attachment portions 41, 45 to connect and/or to disconnect. Accordingly, a resilience towards deformation of the attachment portions 41, 45 provides a first detachment force.

In embodiments, the first attachment portion and/or the second attachment portion are less mechanically flexible than the first and second base portions. Thereby, the less mechanically flexible first and/or second attachment portions provide a larger detachment force because they are more resilient towards deformations.

In embodiments, the second attachment portion comprises a resilient coupling member. In one embodiment, the resilient coupling member comprises a depression. In one embodiment, the first attachment portion comprises a protrusion. In one embodiment, the protrusion is configured to fit into the depression of the resilient coupling member to provide a first detachment force when fitted into the depression.

In embodiments, the depression and protrusion each constitute a mating part configured to form a mating connection. This improves the attachment between the attachment portions and the sealing properties of the connected first and second coupling parts. During a change from being disconnected to being connected the first attachment portion and/or the second attachment portion deform to allow the protrusion to enter the depression. Thereby, a first detachment force is provided by a resilience of the first and second attachment portions towards deformations. The detachment force may then depend on a hardness of the first and second attachment portions.

In embodiments, the first coupling part is arranged on the sealing wafer. The sealing wafer is attached to the skin of the user during normal use. The enclosed volume of air in the first coupling part provides the first coupling part with a larger mechanical flexibility than the second coupling part. In order to improve the ability of the sealing wafer to conform to the shape of the skin, it is advantageous to provide the sealing wafer with the first coupling part and the collecting bag with the second coupling part. This in turn improves the sealing properties of the coupling system.

In embodiments, the enclosed volume of air 10 is at least partially enclosed by a surface of the sealing wafer. This further improves the mechanical flexibility of the sealing wafer and thus the ability of the sealing wafer to conform to the shape of the skin. This provides a more effective seal between the skin and sealing wafer.

In embodiments, the enclosed volume of air 10 is at least partially enclosed by a surface of the collecting bag. This further improves the mechanical flexibility of the first coupling part and the sealing properties of the connected first and second coupling parts.

According to embodiments, the coupling system further comprises a third coupling part and a fourth coupling part, the third and fourth coupling parts being configured to connect and to form a load bearing structure defining a load bearing detachment force when connected. In embodiments, the first coupling part and second coupling part form a sealing structure defining a sealing detachment force when connected. In embodiments, the load bearing detachment force is greater than the sealing detachment force.

Thereby, the first and second coupling parts are relieved from carrying any significant load as the load (caused by the weight of stomal output in the collecting bag) is substantially carried by the third and fourth coupling parts. In one embodiment, the third and fourth coupling parts are configured to carry at least 70 percent of the load, more particularly at least 80 percent of the load, more particularly at least 90 percent of the load, more particularly at least 95 percent of the load. This enables the first and second coupling parts to be designed and configured with little or no regard to their load bearing capabilities. This provides a solution in which the sealing properties of the first and second coupling parts can be optimized for sealing, as the first and second coupling parts do not need to carry any significant load. This allows for the first and second coupling parts to have greater mechanical flexibility to efficiently allow the coupling parts to form a seal and conform to movements of the user. Accordingly, by providing a system with two pairs of coupling parts with each their designated role, i.e. the first and the second coupling parts providing good sealing properties and the third and fourth coupling parts providing good load bearing properties, both the sealing properties and the load bearing properties of the coupling system are improved.

In the embodiment of FIG. 1, the coupling system further includes a third coupling part 29 and a fourth coupling part 31. The third and fourth coupling parts 29, 31 are configured to form a load bearing structure defining a load bearing detachment force when connected. In alternative embodiments, the coupling system 3 does not include the third and fourth coupling parts 29, 31, in which case the first and second coupling parts 9, 11 may be configured to carry the load of the collecting bag.

In the embodiment of FIG. 1, the first and second coupling parts 9, 11 form a sealing structure defining a sealing detachment force. In embodiments, the load bearing detachment force of the load bearing structure is greater than the sealing detachment force of the first and second coupling parts. In one embodiment, the second coupling part 11 is attached to the collecting bag via a foldable connection 50. Thereby, the second coupling part 11 can be said to floatingly connect the collecting bag 7 to the sealing wafer 5. By 'floatingly connect' is meant that the collecting bag 7 is connected to the sealing wafer 5 such that movement of the collecting bag 7 relative to the sealing wafer 5, does not cause an immediate, relative movement of the proximal wall 21 of the collecting bag 7. In other words, the foldable connection 50 allows movement of the collecting bag 7 relative to the sealing wafer 5 as long as the foldable connection 50 is not fully extended.

In embodiments, the third and fourth coupling parts 27, 31 of the load bearing structure are configured to allow less relative movement of the collecting bag 7 and sealing wafer 5, than the first and second coupling parts 9, 11. Accordingly, the load bearing structure will experience strain before the sealing structure. Thus, the sealing structure may be relieved from load bearing. In the embodiment of FIG. 1, the fourth coupling part 31 is attached to the collecting bag 7 and includes an adhesive on a proximal side. The adhesive on the fourth coupling part 31 attaches to the sealing wafer 5. In this case, the third coupling part 29 forms part of the sealing wafer 5. In embodiments, the third and fourth coupling parts 29, 31 are arranged radially outward of the first and second coupling parts 9, 11 in relation to the stoma-receiving openings 18, 27.

Figure 5:
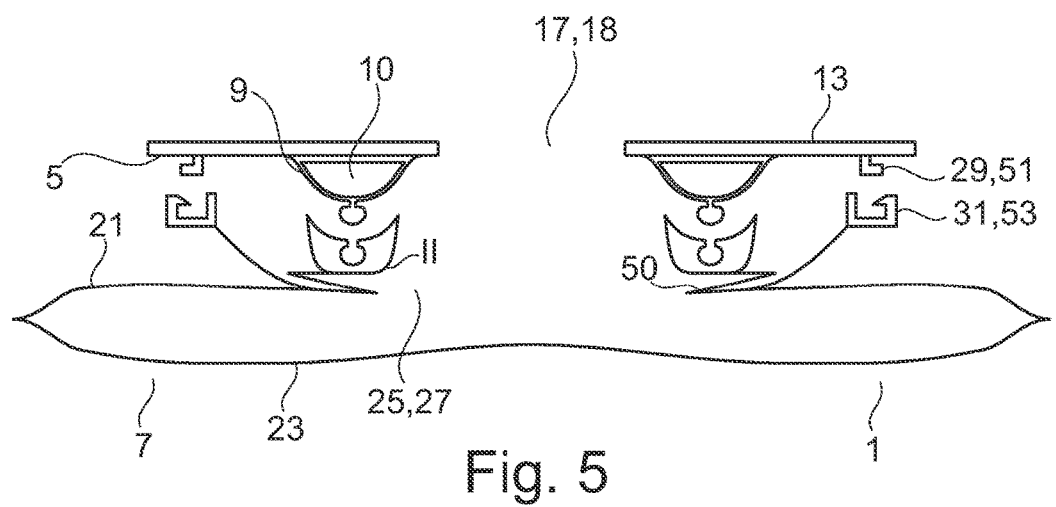
FIG. 5 illustrates a schematic cross-sectional side view of an embodiment of an ostomy appliance.

FIG. 5 illustrates a schematic cross-sectional side view of an embodiment of an ostomy appliance 1 with a coupling system 3. In the embodiment illustrated in FIG. 5, the third and fourth coupling parts 29, 31 form a load bearing structure defining a load bearing detachment force. In FIG. 5, the third and fourth coupling parts 29, 31 are illustrated to include resilient coupling members 51, 53. In one embodiment, the resilient coupling members 51, 53 are configured to deform in order for the first and second coupling parts 29, 31 to connect and to disconnect. In embodiments, the third and fourth coupling parts 29, 31 are significantly easier to connect than to disconnect. In embodiments, a hardness of the resilient coupling members 51, 53 is significantly larger than a hardness of the first and second coupling parts 9, 11 forming a sealing structure defining a sealing detachment force. Accordingly, in embodiments the load bearing detachment force is significantly larger than the sealing detachment force. In embodiments, the third and fourth coupling members 29, 31 are configured to detachably connect or fixedly connect. In embodiments that include the shapes illustrated in FIG. 5, the detachment force may be varied by varying the hardness of the resilient coupling members 51, 53.

In embodiments, the first coupling part is arranged radially closer to the stoma-receiving opening than the third coupling part. In embodiments, the second coupling part is arranged radially closer to the stoma-receiving opening than the fourth coupling part. Thereby, a sealing structure formed by the first and second coupling parts locates between the stoma-receiving openings and the load bearing structure formed by the third and fourth coupling parts. Accordingly, the sealing structure prevents visceral content from reaching the load bearing structure. In embodiments, the materials of the load bearing structure are allowed to be less resistant towards visceral content than materials of the sealing structure.

In embodiments, the third and fourth coupling parts are configured to detachably connect. This is particularly advantageous if the first and second coupling parts are also configured to detachably connect. The user may then leave the sealing wafer on while changing the collecting bag.

In embodiments, the third and fourth coupling parts are configured to fixedly connect. In embodiments, this enables the load bearing structure formed by the third and fourth coupling parts to define a larger load bearing detachment force, as disconnection capability is not needed.

In embodiments, the first coupling part and the third coupling part are separate parts, and/or the second coupling part and the fourth coupling part are separate parts. In embodiments, 'separate parts' should be understood to mean that the parts are provided at a distance from each other without being in direct physical contact, albeit being interconnected.

In embodiments, the first and third coupling parts are arranged on either the collecting bag or the sealing wafer, i.e. the first and third coupling parts are arranged on the collecting bag or the first and third coupling parts are arranged on the sealing wafer. In embodiments, wherein the first and third coupling parts are arranged on the collecting bag, the second and fourth coupling parts are arranged on the one of the sealing wafer and vice versa. In embodiment, the first and third coupling parts are designed and arranged independent of the second and fourth coupling parts. This provides a coupling system having improved sealing and load bearing properties.

In another aspect, embodiments provide a coupling system for an ostomy appliance comprising a collecting bag, the coupling system comprising:

a sealing coupling part encircling a stoma-receiving opening, and comprising a proximal surface for facing a user's skin and a distal surface for facing away from the user;

a load-bearing coupling part encircling a stoma-receiving opening, and comprising a proximal surface for facing the distal surface of the sealing coupling part and a distal surface for facing the collecting bag, wherein the load-bearing coupling part comprises an extension for connecting to the user's body radially offset from the sealing coupling part; and a connecting structure for interconnecting the sealing coupling part and the load-bearing coupling part.

In embodiments, the sealing coupling part is configured to attach to the user's skin via the proximal surface of the sealing coupling part. In embodiments, the proximal surface of the sealing coupling part comprises an adhesive or a sealing mating part. In embodiments, the load-bearing coupling part is arranged on the collecting bag. In embodiments, the extension for connecting to the user's body is connected directly to the user's body by an adhesive on the extension. In embodiments, the extension connects to the user's body via the distal surface of a wafer, the wafer at least partly surrounding the sealing coupling part. In embodiments, the extension connects to the wafer by an adhesive on the wafer and/or the extension. In embodiments, the extension connects to the wafer via mating parts on either surface configured to form a mechanical mating connection, One suitable mechanical mating connection could e.g. be in the form of Velcro.

In embodiments, the sealing coupling part comprises an enclosed volume of air.

In embodiments, the connecting structure is arranged on the proximal surface of the load bearing coupling part. In embodiments, an adhesive or a mating part forms a mechanical mating connection with a sealing mating part of the sealing coupling part.

By connecting the extension of the load-bearing coupling part to the user's skin, or a wafer on the user's skin, without connecting it to the sealing coupling part, the sealing coupling part may be relieved from carrying any significant load as this load is carried by load-bearing coupling part. This enables the sealing coupling part to be designed and configured with little or no constraints in terms of load bearing capabilities. This provides improved sealing properties, as the sealing coupling part does not need to carry any significant load.

Figure 6:
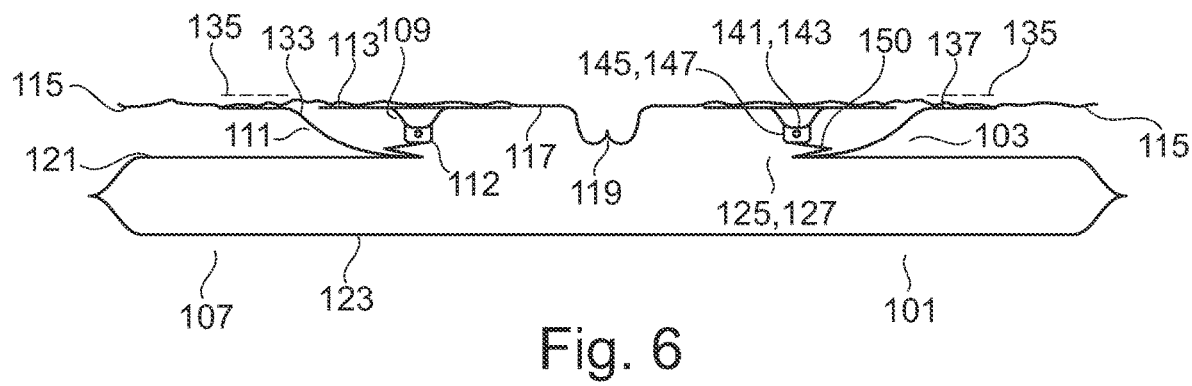
FIG. 6 illustrates a schematic cross-sectional side view of an embodiment of an ostomy appliance.

FIG. 6 illustrates a schematic cross-sectional side view of an embodiment of an ostomy appliance 101 with a coupling system 103 for attaching a collecting bag 107 to a user. In embodiments, the coupling system 103 comprises a sealing coupling part 109, a load bearing coupling part 111 and a connecting structure 112.

In embodiments, the sealing coupling part 109 defines a proximal surface 113 provided with an adhesive adapted for engagement to a skin surface 115 of a user and therefore presents with skin-friendly characteristics. The sealing coupling part 109 defines a stoma-receiving opening 117. In one embodiment, the sealing coupling part 109 is adapted to allow the stoma-receiving opening 117 to be customized to a size and shape of a user's individual stoma 119.

The collecting bag 107 includes a proximal wall 121 and a distal wall 123, The collecting bag 107 includes an inlet opening 125 in the proximal wall 121 of the collecting bag 107 for receiving stomal output. The inlet opening 125 coincides with a stoma-receiving opening 127 of the load bearing coupling part 111.

In embodiments, the load-bearing coupling part 111 includes an extension 133 for connecting to the user's body in an area marked by the dashed lines 135 radially offset from the sealing coupling part 109, In embodiments, the extension 133 connects directly to the skin 115 of the user's body by way of an adhesive on a proximal surface 137 of the extension 133.

In embodiments, the connecting structure 112 includes a first attachment portion 141 in the form of a resilient coupling member including a protrusion 143, and a second attachment portion 145 in the form of a resilient coupling member including a depression 147 formed in the resilient coupling member. In embodiments, the first and second attachment portions 141, 145 are configured to deform in order for the attachment portions to connect and disconnect. Accordingly, a resilience towards deformation of the attachment portions 141, 145 can be said to provide a sealing detachment force. In embodiments, the connecting structure includes a foldable extension 150, which in one embodiment allows some movement of the sealing coupling part 109 relative to the load bearing coupling part 111.

The invention claimed is:

1. An ostomy appliance coupling system comprising:
a sealing wafer having a proximal surface adapted to attach to skin, a distal surface opposite of the proximal surface, and a stoma-receiving opening formed through a thickness of the sealing wafer;
an ostomy bag having a proximal wall, an opposite distal wall, and a waste inlet opening formed in the proximal wall of the ostomy bag;
a first coupling part comprising a gas-impermeable layer forming an enclosed volume of air, with the gas-impermeable layer sealed to one of the distal surface of the sealing wafer and the proximal surface of the ostomy bag to prevent escape of the enclosed volume of air from the ostomy appliance, and the first coupling part comprising a protruding member; and
a second coupling part connected to an opposite one of the distal surface of the sealing wafer and the proximal surface of the ostomy bag, with the second coupling part comprising a depression adapted to receive and couple with the protruding member of the first coupling part to removably couple the ostomy bag to the sealing wafer.

2. The ostomy appliance coupling system of claim 1, wherein the first coupling part encircles the stoma-receiving opening of the sealing wafer and the second coupling part encircles the waste inlet opening of the ostomy bag.

3. The ostomy appliance coupling system of claim 1, wherein the first coupling part comprises:
a first base portion sealed to one of the distal surface of the sealing wafer and the proximal surface of the ostomy bag;
a second base portion sealed to another of the distal surface of the sealing wafer and the proximal surface of the ostomy bag; and
wherein the gas-impermeable layer is connected between the first base portion and the second base portion to form the enclosed volume of air sealed relative to one of the distal surface of the sealing wafer and the proximal surface of the ostomy bag.

4. The ostomy appliance coupling system of claim 3, wherein the first base portion is radially closer to a respective one of the stoma-receiving opening and the waste inlet opening than is the second base portion.

5. The ostomy appliance coupling system of claim 1, wherein the first coupling part and the second coupling part form a gas impermeable seal and a liquid impermeable seal when coupled.

6. The ostomy appliance coupling system of claim 1, wherein the proximal surface of the sealing wafer comprises an adhesive selected from the group consisting of polyisobutylene, styrene-isoprene-styrene, and adhesive including a hydrocolloid.

7. The ostomy appliance coupling system of claim 1, further comprising a first adhesive applied to the distal surface of the sealing wafer and a second adhesive applied to the proximal surface of the ostomy bag;
   wherein the first adhesive and the second adhesive are configured to allow the first coupling part to detachably connect with the second coupling part.

8. The ostomy appliance coupling system of claim 1, wherein the protruding member of the first coupling part is less mechanically flexible than the gas-impermeable layer forming the enclosed volume of air.

9. The ostomy appliance coupling system of claim 1, wherein the second coupling part comprising the depression is less mechanically flexible than the gas-impermeable layer forming the enclosed volume of air.

10. An ostomy appliance coupling system comprising:
    a sealing wafer having an adhesive proximal surface adapted to attach to skin, a distal surface opposite of the adhesive proximal surface, and a stoma-receiving opening formed through a thickness of the sealing wafer;
    an ostomy bag having a proximal wall, an opposite distal wall, and a waste inlet opening formed in the proximal wall of the ostomy bag;
    a first coupling part comprising a gas-impermeable layer forming an enclosed volume of air, with the gas-impermeable layer sealed to the distal surface of the sealing wafer to prevent escape of the enclosed volume of air from the ostomy appliance, and the first coupling part comprising a protruding member; and
    a second coupling part connected to the proximal surface of the ostomy bag, with the second coupling part comprising a depression adapted to receive and couple with the protruding member of the first coupling part to removably couple the ostomy bag to the sealing wafer.

* * * * *